United States Patent [19]

Chang et al.

[11] Patent Number: 5,552,024
[45] Date of Patent: Sep. 3, 1996

[54] PROCESS FOR RECOVERING DIPROPYLENE GLYCOL TERT-BUTYL ETHERS

[75] Inventors: Te Chang, West Chester; Stephen H. Harris, Kennett Square, both of Pa.

[73] Assignee: ARCO Chemical Technology, L.P., Greenville, Del.

[21] Appl. No.: 203,162

[22] Filed: Feb. 28, 1994

[51] Int. Cl.$^6$ .................................................. B01D 3/40
[52] U.S. Cl. .................. 203/64; 203/78; 203/80; 203/DIG. 16; 568/697; 568/699
[58] Field of Search ................. 203/64, 78, 80, 203/DIG. 16; 568/697, 699

[56] References Cited

U.S. PATENT DOCUMENTS

| | | | |
|---|---|---|---|
| 2,927,064 | 3/1960 | Luzader et al. | 203/64 |
| 3,410,762 | 11/1968 | Dean | 203/64 |
| 3,578,568 | 5/1971 | Washall | 203/64 |
| 3,878,058 | 4/1975 | Tanaka et al. | 203/64 |
| 4,254,246 | 3/1981 | Dicoi et al. | 203/DIG. 6 |
| 4,299,997 | 11/1981 | Matsumoto et al. | 568/678 |
| 4,510,022 | 4/1985 | Berg et al. | 203/64 |
| 4,551,207 | 11/1985 | Berg et al. | 203/64 |
| 4,585,526 | 4/1986 | Berg et al. | 203/64 |
| 4,666,563 | 5/1987 | Berg et al. | 568/913 |
| 4,675,082 | 6/1987 | Gupta | 568/678 |
| 4,709,101 | 11/1987 | Masilamami et al. | 568/697 |
| 4,855,531 | 8/1989 | Berg | 585/804 |
| 4,897,161 | 1/1990 | Berg et al. | 203/51 |
| 5,152,876 | 10/1992 | Berg et al. | 203/64 |
| 5,160,414 | 11/1992 | Lee et al. | 203/64 |
| 5,160,585 | 11/1992 | Berg | 203/64 |

OTHER PUBLICATIONS

CA 119(12): 119969p.
CA 119(6): 51744d.

*Primary Examiner*—Virginia Manoharan
*Attorney, Agent, or Firm*—Jonathan L. Schuchardt

[57] ABSTRACT

A process for making and purifying dipropylene glycol tert-butyl ethers (DPTB). DPTB is made by reacting dipropylene glycol with isobutylene in the presence of an acidic catalyst. Extractive distillation of the product mixture using a glycol extracting agent, preferably dipropylene glycol, allows removal of di-tert-butyl ether impurities as an overhead product. The DPTB product is then distilled to separate it from the glycol extracting agent. High-purity DPTB, substantially free of diethers and exceptionally useful as a solvent, is obtained from the process.

17 Claims, 1 Drawing Sheet

PROCESS FOR RECOVERING DIPROPYLENE GLYCOL TERT-BUTYL ETHERS

FIELD OF THE INVENTION

The invention relates to a purification process for dipropylene glycol tert-butyl ethers (DPTB), a product available from the acid-catalyzed reaction of dipropylene glycol and isobutylene. In particular, the invention is a distillation process that uses a glycol extracting agent to enable recovery of pure DPTB.

BACKGROUND OF THE INVENTION

Dipropylene glycol tert-butyl ether (DPTB) is a useful solvent for cleaners and coatings because of its excellent solvency power, low odor, good coalescing properties, and relatively low vapor pressure. DPTB can be made by reacting dipropylene glycol with isobutylene in the presence of an acidic catalyst. Crude DPTB made by this method contains unreacted dipropylene glycol and di-tert-butyl ethers derived from dipropylene glycol. DPTB is more volatile than dipropylene glycol, and the two can be separated successfully by ordinary distillation techniques. Di-tert-butyl ethers derived from dipropylene glycol, on the other hand, are not easily separated from DPTB because the compounds have similar boiling ranges.

To minimize the amount of di-tert-butyl ethers generated in the process, DPTB can be prepared using an excess of dipropylene glycol, so that the major separation problem is in isolating DPTB from unreacted dipropylene glycol. The level of di-tert-butyl ethers remaining in the DPTB product will then be quite small.

Unfortunately, di-tert-butyl ethers derived from dipropylene glycol are not miscible with water. Consequently, even a low concentration of diether impurities in DPTB significantly impairs water miscibility and makes aqueous mixtures of DPTB appear hazy. Removal of the di-tert-butyl ether impurities is needed to give a DPTB product having satisfactory water miscibility. However, because of the similarity in boiling points between DPTB and the di-tert-butyl ether impurities, purification by ordinary distillation is impracticable.

Extractive distillation is often used to separate compounds having similar boiling points. In this technique, an extracting agent is included in the distillation process to enhance the boiling point difference between the compounds of interest. For example, Berg et al. (U.S. Pat. No. 4,585,526) teach to separate o-xylene from m-xylene using propoxypropanol as an extractive agent. Although many extractive distillation processes are known, we are unaware of one for separating glycol monoethers from glycol diether impurities.

A way to recover DPTB from mixtures of DPTB and a minor proportion of di-tert-butyl ether impurities derived from dipropylene glycol is needed. Preferably, the process could enhance the purity of DPTB enough to overcome the water miscibility problems created by the presence of the diethers. A preferred process would be easy to practice, and could be coupled with the process for making DPTB from dipropylene glycol and isobutylene.

SUMMARY OF THE INVENTION

The invention is a process for recovering dipropylene glycol tert-butyl ethers (DPTB) from a mixture of DPTB and a minor proportion of di-tert-butyl ether impurities derived from dipropylene glycol. Although DPTB and the di-tert-butyl ether impurities have similar boiling ranges, we surprisingly found that DPTB can be successfully purified of the impurities when the mixture is distilled in an extractive distillation column in the presence of a glycol extracting agent. Useful glycol extracting agents are dipropylene glycol and glycols that have a higher boiling point than dipropylene glycol. The glycol extracting agent is used in an amount effective to permit removal of the di-tert-butyl ether impurities from the mixture as an overhead distillation product. After removal of the di-tert-butyl ether impurities, the mixture is distilled in a product distillation column to recover, as an overhead product, DPTB that is substantially free of di-tert-butyl ether impurities.

The invention includes a process for making and recovering DPTB. In this process, DPTB is first made by reacting dipropylene glycol with isobutylene in the presence of an acidic catalyst. The product mixture, which contains DPTB, unreacted dipropylene glycol, and di-tert-butyl ether impurities, is then purified by extractive distillation using a glycol extracting agent as described above. Thus, the purification process of the invention is conveniently coupled with a process for making DPTB.

A key advantage of the invention is that it enables the preparation of DPTB that is substantially free of di-tert-butyl ether and isobutylene oligomer impurities, and overcomes the water miscibility problems of DPTB made and purified by ordinary techniques. Because dipropylene glycol can be used as the glycol extracting agent, purification is conveniently integrated into a process for making DPTB.

DETAILED DESCRIPTION OF THE INVENTION

Figure 1:
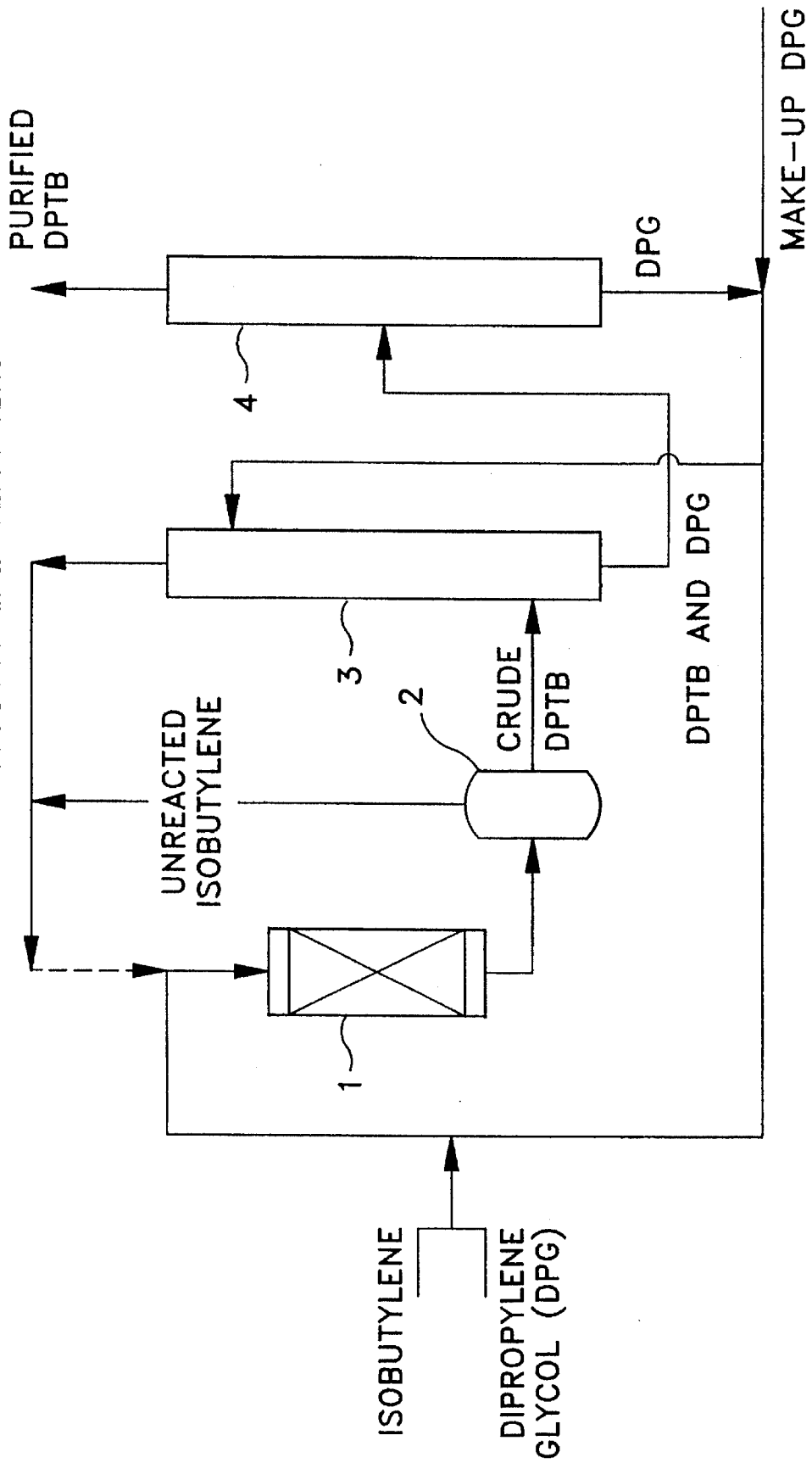
FIG. 1 shows one way of making and recovering dipropylene glycol tert-butyl ethers (DPTB) by the process of the invention. Dipropylene glycol and isobutylene react in acidic resin bed 1. Unreacted isobutylene is recovered by flashing the reactor effluent in flash tank 2. The products are distilled in the presence of added dipropylene glycol (extracting agent) in extractive distillation column 3. Di-tert-butyl ether and isobutylene oligomer impurities are removed overhead and are optionally returned to the acidic resin bed. The extractive column bottoms are redistilled through product column 4 to recover purified DPTB. Dipropylene glycol (DPG) is recovered from the product column and is returned either to the extractive column, the acidic resin bed, or both.

The invention is a process for recovering dipropylene glycol tert-butyl ethers (DPTB). By "DPTB," we mean any mono-tert-butyl ether derived from dipropylene glycol. DPTB can be made by reacting dipropylene glycol with isobutylene under acidic conditions. The resulting product mixture, which contains DPTB, unreacted dipropylene glycol, and di-tert-butyl ether impurities derived from dipropylene glycol, presents a unique separation problem because of the similarity in boiling points of DPTB and the di-tert-butyl ether impurities. When the process is performed using excess dipropylene glycol, only a minor proportion of di-tert-butyl ether impurities will be generated. Since DPTB is separable from dipropylene glycol by simple distillation, the key problem remaining is how to separate the minor proportion of di-tert-butyl ether impurities from DPTB.

Aware that extractive distillation techniques are known for separating compounds having close boiling points, we wondered whether an extracting agent could be found to facilitate the separation of DPTB from the di-tert-butyl ether impurities. Because dipropylene glycol is already part of the process for making DPTB, we first obtained vapor-liquid equilibrium data for mixtures of DPTB, di-tert-butyl ether impurities, and dipropylene glycol.

Our experiments revealed a substantial difference in the relative volatilities of DPTB and di-tert-butyl ether impurities when the liquid-phase concentration of dipropylene glycol in the equilibrium mixture is in excess of about 40 wt. %. Apparently, the difference in the degree of molecular association of dipropylene glycol and DPTB versus the di-tert-butyl ethers becomes significant enough at about 40 wt. % dipropylene glycol to induce a significant boiling point difference between DPTB and the di-tert-butyl ethers. This unexpected observation encouraged us to try using dipropylene glycol as an extracting agent in an extractive distillation process for purifying DPTB.

We found that dipropylene glycol and glycol extracting agents that have a higher boiling point than dipropylene glycol can in fact be successfully used as extracting agents in an extractive distillation process for purifying DPTB. By introducing the glycol extracting agent into the extractive distillation column in an amount effective to permit removal of the di-tert-butyl ether impurities as an overhead distillation product, we are able to obtain DPTB that contains less than about 0.5 wt. % of di-tert-butyl ether impurities. By "overhead" distillation product, we mean a relatively volatile component that can be condensed and removed from a distillation column either as an overhead or as a side-draw product. Surprisingly, the use of a glycol extracting agent also facilitates overhead removal of isobutylene oligomers commonly present in crude DPTB mixtures.

The ability to make high-purity DPTB is an important advantage of the invention because the presence of even low concentrations of di-tert-butyl ethers impairs the usefulness of DPTB as a solvent by interfering with water miscibility. Consequently, unless the di-tert-butyl ether impurities are substantially eliminated, aqueous mixtures containing DPTB will be hazy and unacceptable for many end-uses where clear solutions are desired.

The process of the invention includes two distillation steps. First, DPTB and a minor proportion of di-tert-butyl ether impurities derived from dipropylene glycol are distilled using an extractive distillation column in the presence of a glycol extracting agent. Suitable glycol extracting agents are dipropylene glycol and glycols that have a higher boiling point than dipropylene glycol. More volatile glycols are not generally suitable because DPTB cannot be easily separated as an overhead product from glycols that are more volatile than dipropylene glycol. Suitable glycol extracting agents include, but are not limited to, dipropylene glycol, tripropylene glycol, triethylene glycol, tetrapropylene glycol, and the like. Dipropylene glycol is preferred.

Preferably, the glycol extracting agent is continuously introduced into the extractive distillation column at a point near the top of the column, above where the crude DPTB is introduced. Distillation trays are normally present above the point at which the extracting agent is introduced to avoid glycol losses. The overhead purge includes di-tert-butyl ether impurities derived from dipropylene glycol and also includes any other light impurities such as isobutylene oligomers. The extractive column should have enough trays to achieve the desired degree of separation between DPTB and the di-tert-butyl ether impurities.

The glycol extracting agent is used in an amount effective to permit removal of the di-tert-butyl ether impurities from the mixture as an overhead distillation product. From vapor-liquid equilibrium data, we found that good separation is achieved between DPTB and di-tert-butyl ether impurities when the liquid concentration is at least about 40 wt. % of dipropylene glycol. Thus, it is preferred that the concentration of the refluxing mixture be adjusted to include at least about 40 wt. % of the glycol extracting agent in the liquid on the trays in the extractive distillation column. More preferably, the concentration of the glycol extracting agent in the liquid on the trays in the extractive column will be up to about 80 wt. %.

The extractive distillation is conducted under vacuum. Preferably, the pressure in the extractive column will be within the range of about 10 to about 400 mm Hg. A more preferred range is from about 10 to about 50 mm Hg. The reflux/distillation (R/D) ratio should be high enough to concentrate di-tert-butyl ether impurities in the overhead purge, and to minimize losses of glycol extracting agent. Preferably, the R/D ratio will be greater than about 5.

In a second distillation step, DPTB and the glycol extracting agent, obtained as bottom products from the extractive distillation step, are distilled in a product column to recover, as an overhead product, DPTB that is substantially free of di-tert-butyl ether impurities. Simple distillation can be used to accomplish this separation because the boiling point difference between DPTB and the glycol extracting agent is substantial.

The bottom products from the extractive distillation are preferably fed to the product column near the middle of the column. The product column is also operated under vacuum. Preferably, the pressure in the product column will be within the range of about 10 to about 400 mm Hg. A more preferred range is from about 10 to about 50 mm Hg. The product column should have enough trays to achieve separation between DPTB and the glycol extracting agent. The preferred R/D ratio is at least about 1, and is preferably within the range of about 1 to 20. Glycol extracting agent recovered from the bottom of the product column is recycled back to the extractive distillation column, the reactor for making DPTB, or both.

The invention includes a process for making and recovering dipropylene glycol tert-butyl ethers (DPTB). In this process, dipropylene glycol is reacted with isobutylene in the presence of an acidic catalyst to produce a mixture which comprises DPTB and minor proportions of unreacted dipropylene glycol and di-tert-butyl ether impurities derived from dipropylene glycol. This crude DPTB product mixture is then purified using the two-step distillation process of the invention.

Any suitable acidic catalyst can be used, including mineral acids, organic acids, acidic ion-exchange resins, Lewis acids, and the like. Preferred acids are acidic ion-exchange resins, which are well-suited to a continuous process for making and purifying DPTB.

In a preferred embodiment of the invention, an excess of dipropylene glycol reacts with isobutylene in the presence of an acidic ion-exchange resin to generate a product mixture which comprises unreacted dipropylene glycol, DPTB, and a minor proportion of di-tert-butyl ether impurities derived from dipropylene glycol. The product mixture also may contain some unreacted isobutylene, which is removed by flashing. The crude product mixture is then sent to an extractive distillation column and is distilled. Additional dipropylene glycol is introduced near the top of the column as the extracting agent to continuously provide 40–80 wt. % of dipropylene glycol in the liquid on the trays in the extractive column. Distillation at reduced pressure removes the di-tert-butyl ether impurities and isobutylene oligomers overhead. The overhead products can be discarded, but they are preferably returned to the acidic resin bed where they are at least partially cracked back to isobutylene and dipropylene glycol. The bottom product from the extractive column, which contains DPTB and unreacted dipropylene glycol, is transferred to a product distillation column and is distilled at reduced pressure. Purified DPTB, containing less than about 0.5 wt. % of di-tert-butyl ether impurities, is recovered as an overhead product. Dipropylene glycol recovered from the product distillation is recycled either to the extractive column, the reactor for making DPTB, or both.

The following examples merely illustrate the invention. Those skilled in the art will recognize many variations that are within the spirit of the invention and scope of the claims.

EXAMPLE 1

Vapor-Liquid Equilibrium (VLE) Data

A distilled sample (about 80 g) comprising 97.2 wt. % dipropylene glycol tert-butyl ether (DPTB), 2.4 wt. % di-tert-butyl ether, and 0.4 wt. % dipropylene glycol (DPG) is refluxed in a glass recirculating vapor-liquid equilibrium (VLE) still to obtain VLE samples. Separate VLE runs are conducted at 10 mm Hg and 50 mm Hg. Based on vapor and liquid sample compositions, the relative volatilities of di-tert-butyl ether to DPTB are 0.89 at 10 mm Hg, and 0.81 at 50 mm Hg. The relative volatilities are close to 1, indicating that it is difficult to separate the two components. Eight more VLE runs are conducted at 10 and 50 mm Hg with mixtures of distilled DPTB and DPG, with incremental increases of DPG. Table 1 gives the relative volatility data of di-tert-butyl ether to DPTB. The data clearly indicate that the separability of DPTB and di-tert-butyl ether improves as DPG concentration increases.

TABLE 1

Vapor-Liquid Equilibrium Data for Dipropylene Glycol tert-Butyl Ether (DPTB)/Dipropylene Glycol (DPG) Mixtures

| DPG/Distilled DPTB Ratio | Relative Volatility, di-tert-butyl ether to DPTB | |
|---|---|---|
| | 10 mm Hg | 50 mm Hg |
| 0 | 0.89 | 0.81 |
| 1.2 | 1.03 | 0.99 |
| 1.5 | 1.30 | 1.26 |
| 2.3 | 1.54 | 1.62 |
| 4.3 | 2.10 | 2.05 |

COMPARATIVE EXAMPLE 2

Attempted Purification of DPTB without Extractive Distillation

A sample of DPTB reactor effluent obtained after flashing off unreacted isobutylene is subjected to a two-step continuous distillation intended to remove DPG and di-tert-butyl ethers. The sample contains about 35 wt. % DPTB, 7 wt. % di-tert-butyl ethers, and 58 wt. % DPG. The distillation column is a 2-inch I. D. packed glass column having about 38 theoretical plates. The sample is fed to the column at the 28th theoretical plate from the top at a rate of about 162 g/h. The column pressure at the top is maintained at about 10 mm Hg by vacuum. The reflux ratio (reflux/distillate) is set at 20. The reboiler temperature is about 138° C., and the top temperature is near 93° C. The distillate is fed to a second column having the same configuration and conditions as the first column. The second column top and bottom temperatures are about 93° C. and 116° C., respectively. Distillation results appear in Table 2.

The first distillation successfully removes over 99 wt. % of the dipropylene glycol. The second distillation is intended to remove di-tert-butyl ether impurities from DPTB. However, only about 50 wt. % of the di-tert-butyl ethers are removed because their boiling range is close to that of DPTB. The product purity of the second column distillate is about 90 wt. % DPTB, including 10 wt. % di-tert-butyl ether impurities. This level of purity is not acceptable for most DPTB solvent applications.

TABLE 2

Attempted Purification of Dipropylene Glycol tert-Butyl Ether (DPTB) Without Extractive Distillation

| Component | Feed | | Distillate | | Bottoms | |
|---|---|---|---|---|---|---|
| | g/h | wt. % | g/h | wt. % | g/h | wt. % |
| First Column | | | | | | |
| DPG | 94 | 58.0 | 0.7 | 1.1 | 93.2 | 99.2 |
| DPTB | 57 | 35.0 | 55.9 | 82.2 | 0.8 | 0.8 |
| Diether | 11 | 7.0 | 11.4 | 16.7 | | |
| Total | 162 | 100.0 | 68 | 100.0 | 94 | 100.0 |
| Second Column | | | | | | |
| DPG | 0.7 | 1.1 | 0.3 | 0.5 | 0.5 | 4.0 |
| DPTB | 55.9 | 82.2 | 49.4 | 89.8 | 6.5 | 49.8 |
| Diether | 11.4 | 16.7 | 5.3 | 9.7 | 6.0 | 46.2 |
| Total | 68 | 100.0 | 55 | 100.0 | 13 | 100.0 |

EXAMPLE 3

Purification of DPTB by Extractive Distillation with DPG

A crude DPTB sample identical to the one used in Comparative Example 2 is subjected to extractive distillation with DPG, followed by product distillation to recover purified DPTB as an overhead product. The columns are identical to those used in Example 2. Both columns are operated at 10 mm Hg of pressure. Crude DPTB is fed to the extractive column at a rate of about 126 g/h at the 28th theoretical plate. In addition, pure DPG is introduced to the column at the 5th theoretical plate near the top at a rate of about 189 g/h. The column has a reflux ratio of 5. Concentrated di-tert-butyl ether is obtained as an overhead distillate. The bottoms are fed to the product column to recover DPTB from DPG by distillation. Results appear in Table 3. The product column distillate is DPTB that contains less than 0.5 wt. % of di-tert-butyl ether impurities. The overall DPTB recovery is greater than 95%.

TABLE 3

Purification of Dipropylene Glycol tert-Butyl Ether (DPTB) by Extractive Distillation using DPG as the Extracting Agent

| Component | Solvent Feed g/h | wt. % | Feed g/h | wt. % | Distillate g/h | wt. % | Bottoms g/h | wt. % |
|---|---|---|---|---|---|---|---|---|
| Extractive Column | | | | | | | | |
| DPG | 189 | 100 | 73.1 | 58.0 | 2.4 | 22.1 | 260.0 | 85.5 |
| DPTB | | | 44.1 | 35.0 | 0.2 | 2.1 | 43.8 | 14.4 |
| Diether | | | 8.8 | 7.0 | 8.3 | 75.8 | 0.2 | 0.07 |
| Total | 189 | 100 | 126 | 100.0 | 11 | 100.0 | 304 | 100.0 |
| Product Column | | | | | | | | |
| DPG | | | 260.0 | 85.5 | 0.7 | 1.7 | 258.9 | 99.2 |
| DPTB | | | 43.8 | 14.4 | 42.1 | 97.8 | 2.1 | 0.8 |
| Diether | | | 0.2 | 0.07 | 0.2 | 0.5 | | |
| Total | | | 304 | 100.0 | 43 | 100.0 | 261 | 100.0 |

The preceding examples are meant only as illustrations. The following claims define the scope of the invention.

We claim:

1. A process for recovering dipropylene glycol tert-butyl ethers (DPTB) from a mixture of DPTB and di-tert-butyl ether impurities derived from dipropylene glycol, said process comprising:

(a) distilling a mixture consisting essentially of DPTB and a minor proportion of di-tert-butyl ether impurities derived from dipropylene glycol in an extractive distillation column using an agent consisting essentially of a glycol extracting agent selected from the group consisting of dipropylene glycol, tripropylene glycol, triethylene glycol, and tetrapropylene glycol in an amount effective to maintain at least about 40% of glycol extracting agent in the liquid in the extractive distillation column and to permit removal of the di-tert-butyl ether impurities from the mixture as an overhead distillation product; and (b) distilling the resulting purified DPTB in a product distillation column to recover, as an overhead product, DPTB that is substantially free of di-tert-butyl ether impurities.

2. The process of claim 1 wherein the glycol extracting agent is continuously introduced near the top of the extractive distillation column in step (a).

3. The process of claim 1 wherein the glycol extracting agent is dipropylene glycol.

4. The process of claim 1 wherein the glycol extracting agent is recovered as a bottom product from the distillation in step (b), and is then reused as an extracting agent in step (a).

5. The process of claim 1 wherein each distillation is performed at a reduced pressure within the range of about 10 to about 400 mm Hg.

6. The process of claim 1 wherein the purified DPTB recovered from step (b) contains less than about 0.5 wt. % of di-tert-butyl ether impurities.

7. A process for making and recovering dipropylene glycol tert-butyl ethers (DPTB), said process comprising:

(a) reacting dipropylene glycol with isobutylene in the presence of an acidic catalyst to produce a mixture which consists essentially of DPTB, unreacted dipropylene glycol, and di-tert-butyl ether impurities derived from dipropylene glycol;

(b) distilling the mixture in an extractive distillation column using an agent consisting essentially of a glycol extracting agent selected from the group consisting of dipropylene glycol, tripropylene glycol, triethylene glycol, and tetrapropylene glycol in an amount effective to maintain at least about 40% of glycol extracting agent in the liquid in the extractive distillation column and to permit removal of the di-tert-butyl ether impurities from the mixture as an overhead distillation product; and (c) distilling the resulting purified DPTB in a product distillation column to recover, as an overhead product, DPTB that is substantially free of di-tert-butyl ether impurities.

8. The process of claim 7 wherein the acidic catalyst is an acidic ion-exchange resin.

9. The process of claim 7 wherein the glycol extracting agent is dipropylene glycol.

10. The process of claim 7 wherein the glycol extracting agent is continuously added near the top of the extractive distillation column in step (b).

11. The process of claim 7 wherein the glycol extracting agent is recovered as a bottom product from the distillation in step (c), and is then reused as an extracting agent in step (b).

12. The process of claim 7 wherein the glycol extracting agent is recovered as a bottom product from the distillation in step (c), and is then reused as a reactant in step (a).

13. The process of claim 7 wherein each distillation is performed at a reduced pressure within the range of about 10 to about 400 mm Hg.

14. The process of claim 7 wherein the purified DPTB recovered from step (c) contains less than about 0.5 wt. % of di-tert-butyl ether impurities.

15. A process for making and recovering dipropylene glycol tert-butyl ethers (DPTB), said process comprising:

(a) reacting dipropylene glycol with isobutylene in the presence of an acidic ion-exchange resin to produce a mixture which consists essentially of DPTB, unreacted dipropylene glycol, and di-tert-butyl ether impurities derived from dipropylene glycol;

(b) distilling the mixture in an extractive distillation column using an agent consisting essentially of dipropylene glycol in an amount effective to maintain at least about 40 wt. % of dipropylene glycol in the liquid in the extractive column and to permit removal of the di-tert-butyl ether impurities from the mixture as an overhead distillation product; and (c) distilling the resulting purified DPTB in a product distillation column to recover, as an overhead product, DPTB that is substantially free of di-tert-butyl ether impurities.

16. The process of claim 15 wherein dipropylene glycol is recovered as a bottom product from the distillation in step (c), and is then reused as an extracting agent in step (b).

17. The process of claim 15 wherein dipropylene glycol is recovered as a bottom product from the distillation in step (c), and is then reused as a reactant in step (a).

* * * * *